(12) United States Patent
Morgan et al.

(10) Patent No.: US 7,272,448 B1
(45) Date of Patent: Sep. 18, 2007

(54) MEDICAL LEAD FOR PLACEMENT IN THE PERICARDIAL SAC

(75) Inventors: Kevin L. Morgan, Simi Valley, CA (US); Annapurna Karicherla, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 74 days.

(21) Appl. No.: 11/136,786

(22) Filed: May 24, 2005

(51) Int. Cl.
*A61N 1/05* (2006.01)

(52) U.S. Cl. ............... 607/129; 607/119; 607/130; 607/131

(58) Field of Classification Search ........ 600/372–374; 607/115, 119–123, 126–128; 604/20, 21, 604/104–109, 523, 524
See application file for complete search history.

(56) References Cited

U.S. PATENT DOCUMENTS

| 4,865,037 A | 9/1989 | Chin et al. ............... 128/419 D |
| 5,033,477 A | 7/1991 | Chin et al. ............... 128/785 |
| 5,052,407 A | 10/1991 | Hauser et al. ............ 128/786 |
| 5,063,932 A | 11/1991 | Dahl et al. ............... 128/639 |
| 5,176,135 A | 1/1993 | Fain et al. ............... 128/419 D |
| 5,191,901 A | 3/1993 | Dahl et al. ............... 128/786 |
| 5,314,462 A | 5/1994 | Heil, Jr. et al. ............ 607/128 |
| 5,425,756 A | 6/1995 | Heil, Jr. et al. ............ 607/128 |
| 2005/0090870 A1* | 4/2005 | Hine et al. ............... 607/17 |

FOREIGN PATENT DOCUMENTS

EP          0571985 B1    12/1993

* cited by examiner

*Primary Examiner*—Carl Layno (57) ABSTRACT

The lead body of a medical lead comprises a distal end portion carrying at least one electrode for placement in the pericardial sac of a human heart. The distal end portion of the lead body includes a multi-turn section having opposed ends, opposing forces applied to the ends tending to flatten the multi-turn section, the multi-turn section being thereby adapted to be retained within the pericardial sac. The turns of the multi-turn section may become progressively smaller from one end of the section to the other end of the section. The multi-turn section may have, in a relaxed state thereof, a generally conical, helical configuration. The at least one electrode may be carried adjacent to the end of the multi-turn section having the larger turns. Alternatively, the at least one electrode may be carried adjacent to the end of the multi-turn section having the smaller turns.

22 Claims, 9 Drawing Sheets

MEDICAL LEAD FOR PLACEMENT IN THE PERICARDIAL SAC

FIELD OF THE INVENTION

The present invention relates generally to medical leads carrying electrodes for electrically stimulating body tissue and/or for sensing the electrical activity of such tissue. More particularly, the invention relates to medical leads configured for secure placement in the pericardial sac of the human heart.

BACKGROUND OF THE INVENTION

Pacemaker leads form the electrical connection between a cardiac pacemaker pulse generator and the heart tissue that is to be stimulated. As is well known, the leads connecting such pacemakers with the heart may be used for pacing or for sensing electrical signals produced by the heart or for both pacing and sensing in which case a single lead serves as a bidirectional pulse transmission link between the pacemaker and the heart. The lead typically comprises a distal end portion carrying a tip electrode and a ring electrode. The lead may also carry one or more cardioverting and/or defibrillating electrodes proximal of the ring electrode.

Various lead types for different placement approaches have been developed. Thus, an endocardial type lead is one that is inserted into a vein and guided therethrough into a cavity of the heart. The distal end of an endocardial lead may carry a helical, screw-in tip element, electrically active or inactive, and/or outwardly projecting tines or nubs for anchoring the lead.

Epicardial or myocardial type leads are attached directly to the epicardium using sutures or another fixation mechanism such as a helical screw-in electrode that engages the myocardium. Myocardial leads typically are used for temporary pacing or for permanent pacing following open-heart surgery. Conventional approaches to the placement of current myocardial leads usually involve thoracotomies. Such placement techniques have disadvantages including the relatively large incisions needed to gain access to the thoracic cavity and to the heart; the difficulty of quickly and easily attaching the lead; the high rate of patient morbidity, trauma and pain; the tendency to require longer in-patient recovery times; and the unattractiveness of the scars left by the procedure.

To mitigate these disadvantages, minimally invasive lead placement systems have been developed for placing a screw-in myocardial lead on the surface of the heart via a small, finger size opening in the chest. Such systems may include a fiberoptics video camera of the type commonly used in other thoracic surgeries (for example, lung biopsies and other thoracic cavity and cardiac procedures) for visually imaging, and thereby aiding, the lead placement procedure. These minimally invasive lead placement systems allow for faster, safer and easier myocardial lead placements with significantly less morbidity, trauma and pain to the patient.

Another example of a minimally invasive lead placement system is found in U.S. Pat. No. 5,052,407. That patent discloses a lead including an electrically active distal region having a preformed, planar, spiral configuration. Using a stylet or guide wire, the distal region of the lead is maneuvered into the pericardial sac of the heart through a small needle puncture in the sac's outer membrane or layer. Once the distal region of the lead is inside the pericardial sac, the stylet or guide wire used to place the lead is withdrawn. As the stylet or guide wire is retracted, the turns of the spiral form in succession within the sac. The relatively large diameter spiral tends to keep the distal region from backing out of the sac without the spiral straightening out, lending a certain degree of stability to the lead. Nevertheless, still further improvement in the anchoring of such lead types would be desirable.

SUMMARY

In accordance with one specific, exemplary embodiment, there is provided a medical lead body comprising a distal end portion carrying at least one electrode for placement in the pericardial sac of a human heart. The distal end portion of the lead body includes a multi-turn section having opposed ends, opposing forces applied to the ends tending to flatten the multi-turn section, the multi-turn section being thereby adapted for placement and retention within the pericardial sac.

Further, the at least one electrode may be carried adjacent to the end of the multi-turn section having the larger turns. Alternatively, the at least one electrode may be carried adjacent to the end of the multi-turn section having the smaller turns.

BRIEF DESCRIPTION OF THE DRAWINGS

The foregoing and other objects, features and advantages of the invention will become evident to those skilled in the art from the detailed description of the preferred embodiments, below, taken together with the accompanying drawings, in which.

DETAILED DESCRIPTION

The following description presents preferred embodiments of the invention representing the best mode contemplated for practicing the invention. This description is not to be taken in a limiting sense but is made merely for the purpose of describing the general principles of the invention whose scope is defined by the appended claims.

Figure 1:
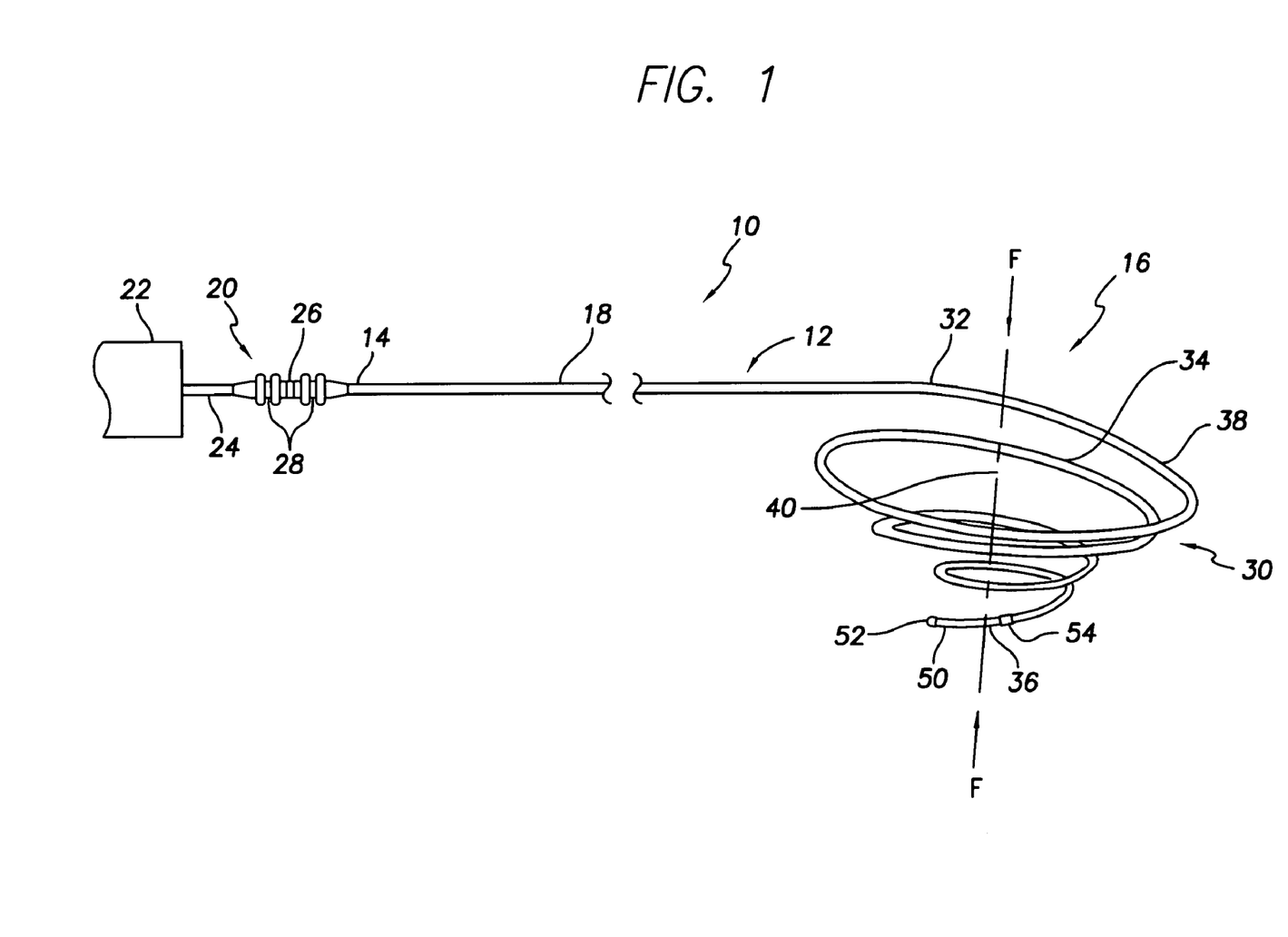
FIG. 1 is a perspective view of a bipolar pacing lead in accordance with one specific exemplary embodiment of the invention.
Figure 2:
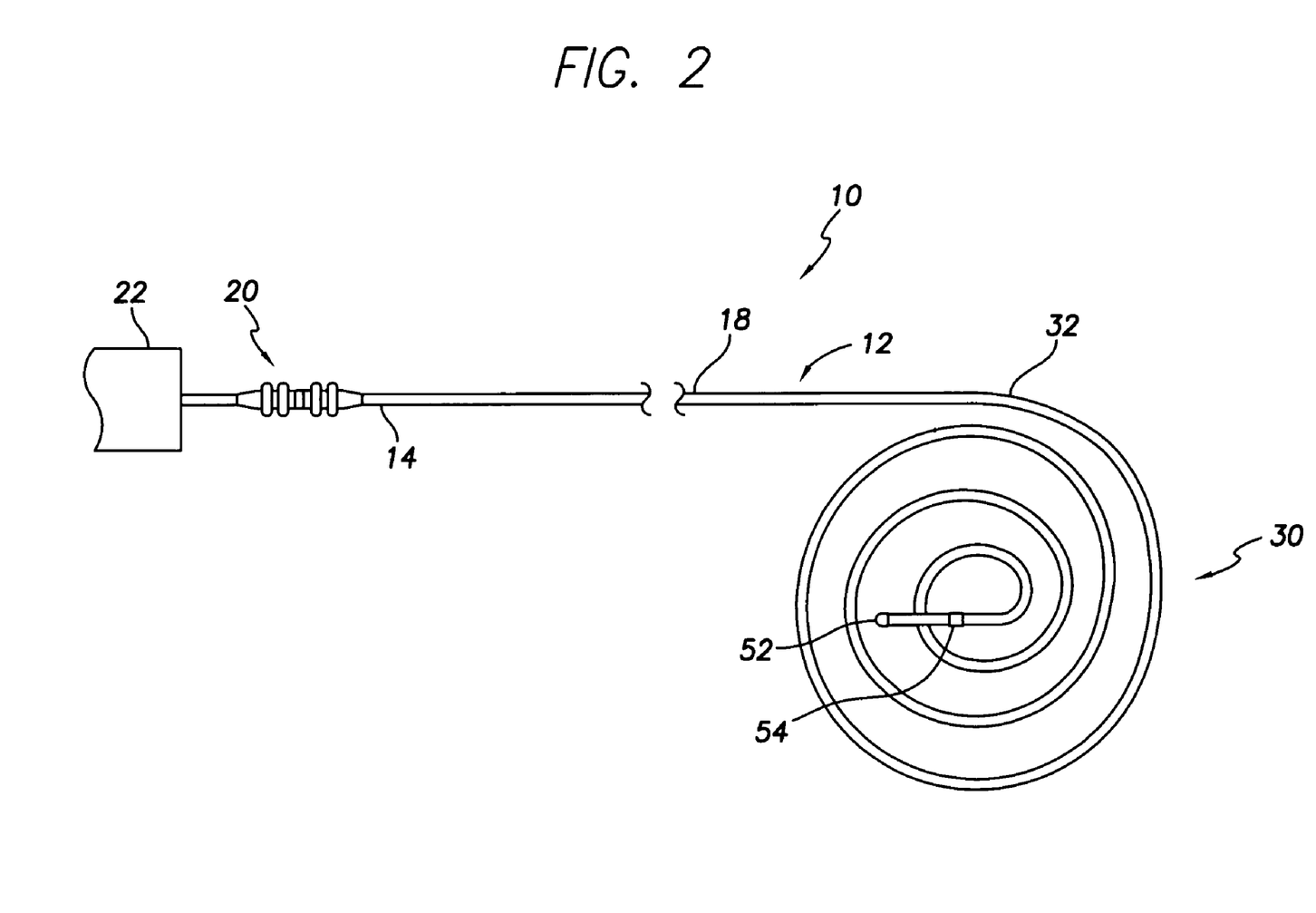
FIG. 2 is a top plan view of the lead shown in FIG. 1.
Figure 3:
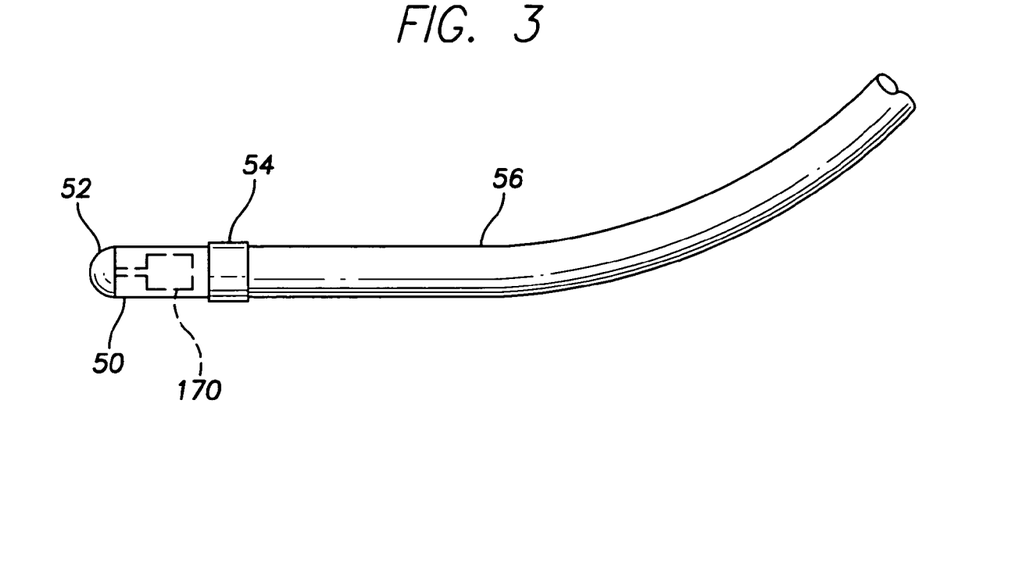
FIG. 3 is a side view of a part of the distal end portion of the lead shown in FIGS. 1 and 2.

FIGS. 1-3 show a medical lead 10 in accordance with a preferred embodiment of the invention. The lead 10 includes a lead body 12 having a proximal end 14, a distal end portion 16 and an intermediate portion 18 between the proximal end and distal end portion. The proximal end 14 of the lead body incorporates a connector assembly 20 that may be compatible with a medical device connector standard such as the IS-1 standard or the proposed IS-4 standard for connecting the lead body 12 to a pacemaker and/or implantable cardioverter-defibrillator (ICD) 22. The connector assembly 20 may include a tubular pin terminal contact 24 and an annular terminal contact 26 electrically coupled to electrodes along the distal end portion of the lead body. The connector assembly 20 of the lead is received within a receptacle of the unit 22 and, as is well known in the art, to prevent ingress of body fluids into the receptacle, the connector assembly 20 may be provided with spaced sets of seals 28. In accordance with well known lead placement techniques, a stylet or guide wire for delivering and steering the distal end portion 16 of the lead body 12 during placement is inserted into a lumen of the lead body through the tubular pin terminal contact 24.

The distal end portion 16 of the lead body in FIG. 1 includes a multi-turn or wound distal section 30 configured for secure placement within the pericardial sac of the heart. The intermediate portion 18 of the lead body has a distal end 32 from which the wound distal section 30 extends. The distal wound section 30 assumes, in a relaxed or unrestrained state, a generally conical, preferably truncated, helical configuration that in plan view (FIG. 2) generally resembles a spiral. The wound section 30 has opposed, first and second ends 34 and 36, respectively, and comprises a plurality of turns 38 about an axis 40 extending through the ends 34 and 36, the sizes of the turns becoming progressively smaller as they proceed from the first end 34 attached to the distal end 32 of the intermediate portion 18 to the second, free end 36. The wound section 30 thus comprises a generally coil spring-like structure so that opposed forces (F, in FIG. 1) applied to the ends 34 and 36 of the section 30 will tend to compress and flatten the section against opposing reaction forces tending to restore the section 30 to its relaxed state. It will be appreciated that the geometry of the turns of the wound section need not, and in practice will unlikely, conform to some mathematical ideal and indeed may depart considerably therefrom. Thus, such terms as "conical", "helical", "spiral" and "axis" are used herein only to facilitate the description of the invention.

The distal end portion 16 of the lead body 12 terminates at a distal extremity 50 incorporating an electrical stimulating and/or sensing tip electrode 52 adapted to be placed in electrical contact or in electrical communication with the tissue to be electrically stimulated and/or sensed. The distal end portion 16 also carries a ring electrode 54 positioned proximally of the tip electrode 52. The ring electrode 54, typically providing a sensing function, is adapted, like the tip electrode, to be placed so as to contact or otherwise electrically communicate with the heart tissue to be stimulated and/or sensed. The lead body 12 may further comprise an outer polymer tube or housing 56 enclosing electrical conductors connecting the lead's electrodes with the terminal contacts on the connector assembly 20.

Figure 4:
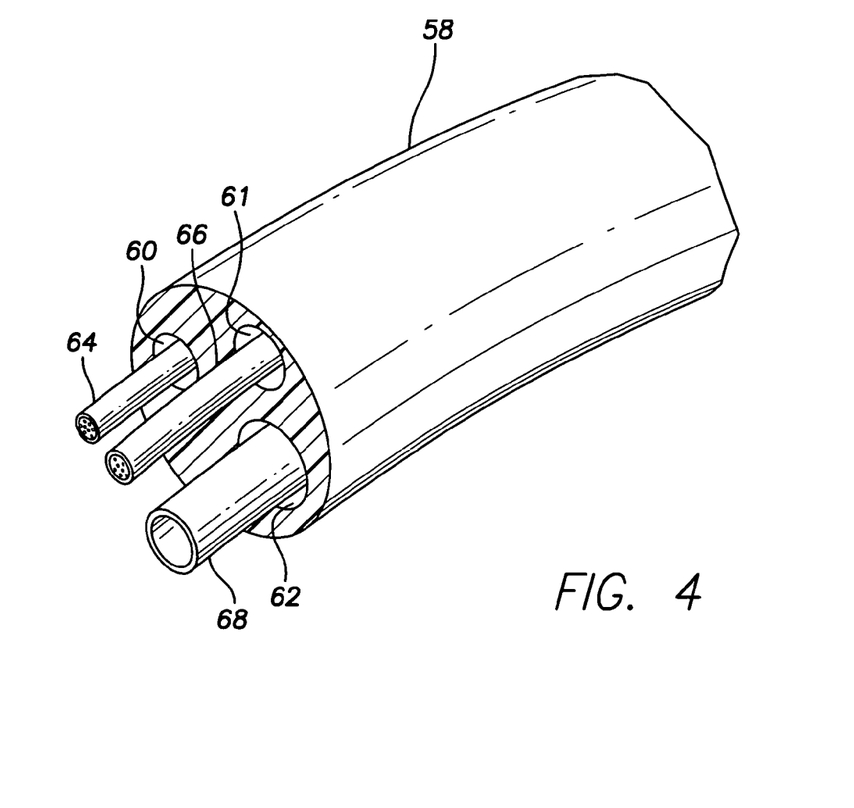
FIG. 4 is a perspective, cutaway view of a portion of a polymer housing that may form part of a lead in accordance with the invention.

In this connection, FIG. 4 shows, by way of example, a multi-lumen housing 58 of silicone rubber, polyurethane, or other biostable, biocompatible polymer defining three parallel, longitudinally extending lumens 60-62 one of which (lumen 62) is preferably larger in diameter than the remaining two. A first cable conductor 64, contained within the lumen 60, electrically connects the tip electrode 52 with the pin terminal contact 24 on the connector assembly 20. A second cable conductor 66 carried within the lumen 61 electrically connects the ring electrode 54 with the annular contact 26 on the connector assembly. The third, larger diameter lumen 62 may enclose a thin walled PTFE tube or liner 68 for receiving a guide wire or stylet for guiding and placing the distal end portion 16 of the lead in a target position within the pericardial sac. Such a multi-lumen housing structure and the use of cable conductors as well as the polymer guide tube or liner for receiving a guide wire or stylet are all well known in the art.

The generally conical helical configuration of the wound section 30 of the distal end portion of the lead body in its relaxed or unrestrained state may be preformed by appropriately heat treating the distal end portions of one or both cables 64 and 66, or by preforming the polymer housing 58, or by both preforming the housing and one or both cable conductors into the desired shape; these techniques are well known in the medical lead art.

Figure 5:
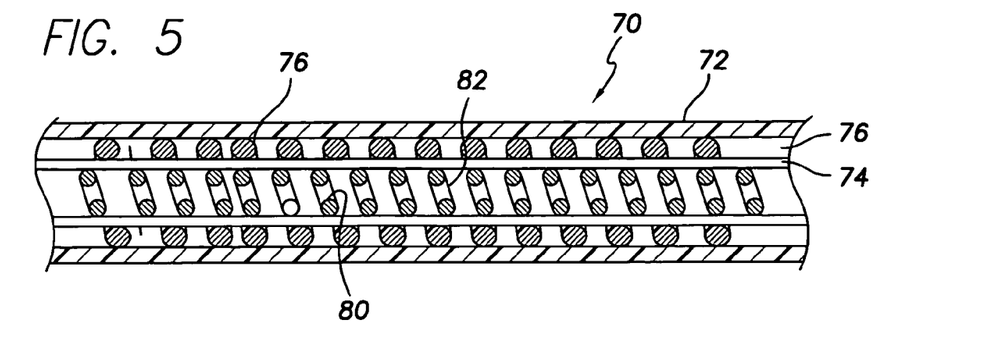
FIG. 5 is an axial cross-section of a portion of a lead having an alternative structure to that shown in FIG. 4.

As an alternative to the housing 58 shown in FIG. 4, there is shown in FIG. 5 a polymer lead body housing 70 comprising coaxial, outer and inner polymer tubes 72 and 74, respectively, defining between them an annular space 76. Contained within the annular space 76 is a first or outer electrical coil conductor 78 connecting one of the electrodes, preferably the ring electrode 54, with the annular terminal contact 26 on the connector assembly 20. A second electrically conductive coil conductor 80 is disposed within the inner tube 74 for connecting the tip electrode 52 with the pin terminal contact 24 on the connector assembly. The generally conical helical configuration of the wound section 30 may be formed by appropriate, conventional heat treatment of the outer and/or inner coil conductors 78, 80 either by themselves or in combination with appropriate performing of the outer and/or inner housing tubes 72, 74. The inner coil conductor 80 defines a lumen 82 that may contain a low friction liner (not shown) of PTFE or the like, for receiving a guide wire or stylet for maneuvering the distal end portion into position within the pericardial sac.

Figure 6:
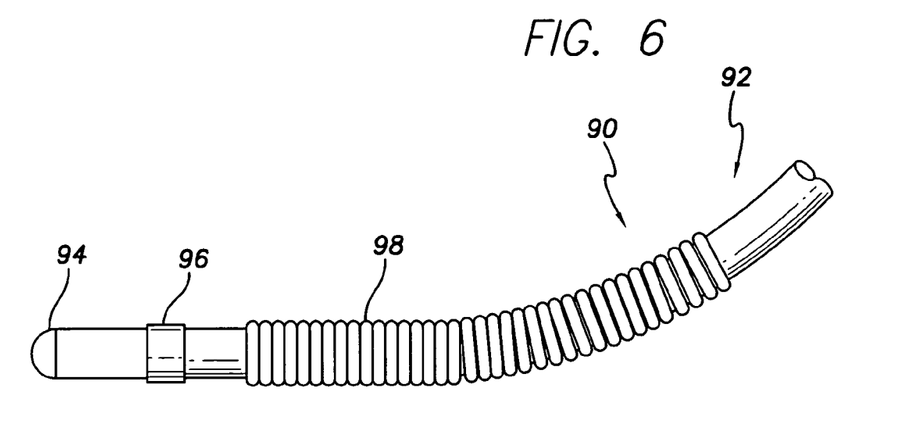
FIG. 6 is a side view of a part of a distal end portion of a lead in accordance with an alternative embodiment of the invention.

Other electrode configurations may be employed. For example, an alternative arrangement may include additional ring stimulation and/or sensing electrodes, as well as one or more cardioverting and/or defibrillating shocking electrodes. For example, FIG. 6 shows a part of a distal end portion 90 of a lead body 92 in accordance with an alternative embodiment of the invention. The distal end portion 90 carries a tip electrode 94 and a ring electrode 96, as described, along with a shocking electrode 98 disposed proximally of the ring electrode 96. The shocking electrode 98 may have a conventional structure, comprising, for example, a wire coil, as shown, or an electrically conductive polymer. A conductive polymer shocking electrode imparts greater flexibility allowing the distal end portion of the lead to be subjected to sharper bends and, because of less tissue ingrowth, to facilitate explantation. The kind of electrode configuration used will depend on the particular application and accordingly any electrode configuration now known in the art or developed in the future may be utilized. In summary, the distal end portion of a lead in accordance with the invention may carry one or more electrodes whose configurations, functions and placement along the length of the distal end portion will be dictated by the indicated stimulation therapy, the peculiarities of the patient's anatomy, and so forth. The electrode(s) may be located anywhere along the length of the distal end portion of the lead body; the electrode(s) are preferably positioned along the distal end portion's length so that the electrode(s) will be disposed within the pericardial sac when the distal end portion is in its final position relative to the body tissue to be electrically stimulated or sensed. The leads shown herein only illustrate examples of the various combinations of stimulating and/or sensing electrodes that may be utilized.

Figure 7:
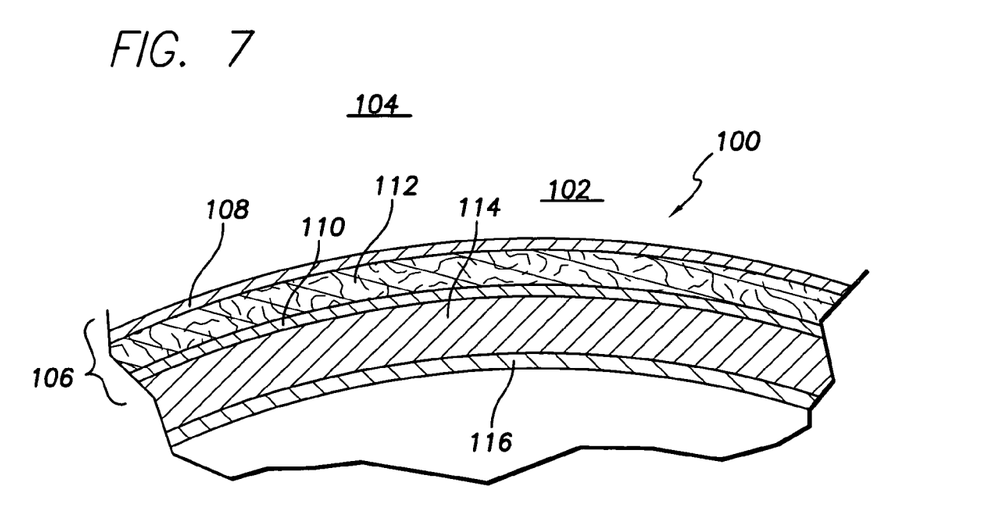
FIG. 7 is a schematic, cross-section view of a portion of the human heart.

With reference to FIG. 7, there is shown in schematic form a portion of a human heart 100. The human heart is a muscular organ located within the pericardial cavity 102 that forms part of the thoracic cavity 104. The heart 100 is enclosed by a fibrous sac 106, called the pericardium or pericardial sac that lines the pericardial cavity 102. The pericardial sac 106 comprises two membranes or layers—an outer layer 108 and an inner layer 110—containing between them a lubricious fluid 112 facilitating movement of the heart as it contracts and expands. The sac's inner layer 110 or epicardium forms the outer lining of the heart wall. The heart wall further has a middle layer 114, the myocardium, consisting of thick bands of muscular tissue as well as a third layer 116, the endocardium, a thin, single layer covering the heart valves and lining the heart cavities.

Figure 8:
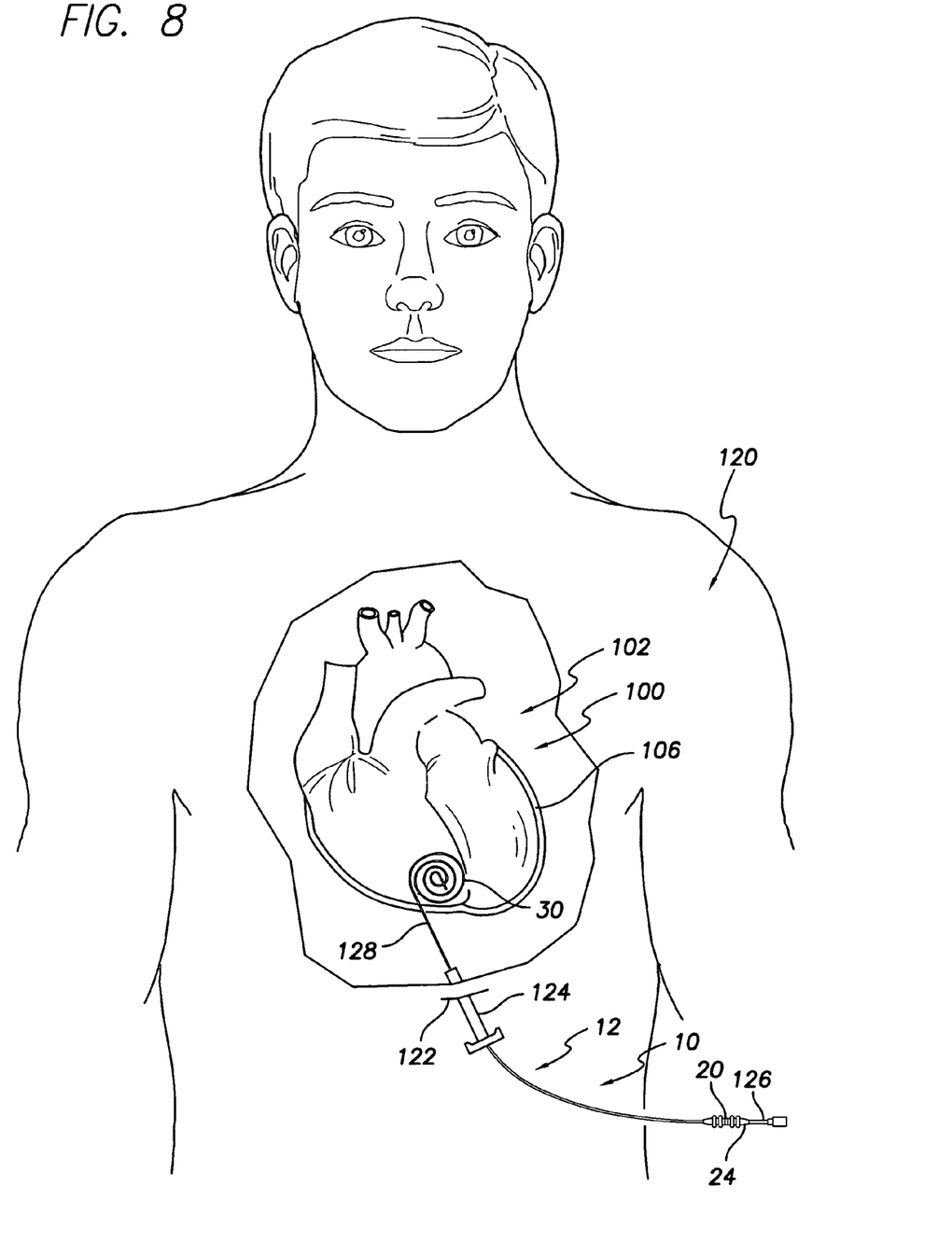
FIG. 8 is a simplified front perspective view of the upper chest region of a human body showing the placement of a lead in accordance with the present invention in the pericardial sac of the heart.

Using the lead structure of FIGS. 1-4 as an example, FIG. 8 illustrates schematically a patient's upper chest region 120 having formed therein a single, small or keyhole intercostal incision 122 for receiving an introducer 124 for guiding the distal end portion 16 of the lead body 12 into the pericardial sac 106 of the heart 100. This minimally invasive technique requires only a single incision the precise location and size of which will vary depending upon the patient's anatomy and the surgeon's preferences. The incision 122 may accommodate a trocar (not shown) for facilitating the insertion and manipulation of the introducer 124. The introduction, maneuvering and placement of the distal end portion 16 of the lead body may be monitored through a conventional fluoroscope or other imaging apparatus (not shown).

The distal end portion 16 of the lead body has a wound section 30 preformed, as already explained, to assume a generally conical, helical configuration in the unrestrained or relaxed state. Prior to the insertion of the lead body into the introducer 124, a stylet or guide wire 126 is passed through the tubular electrical pin 24 at the proximal end of the lead into the PTFE liner 68 in the lumen 62 and advanced so as to straighten the preformed wound section 30.

Figure 9:
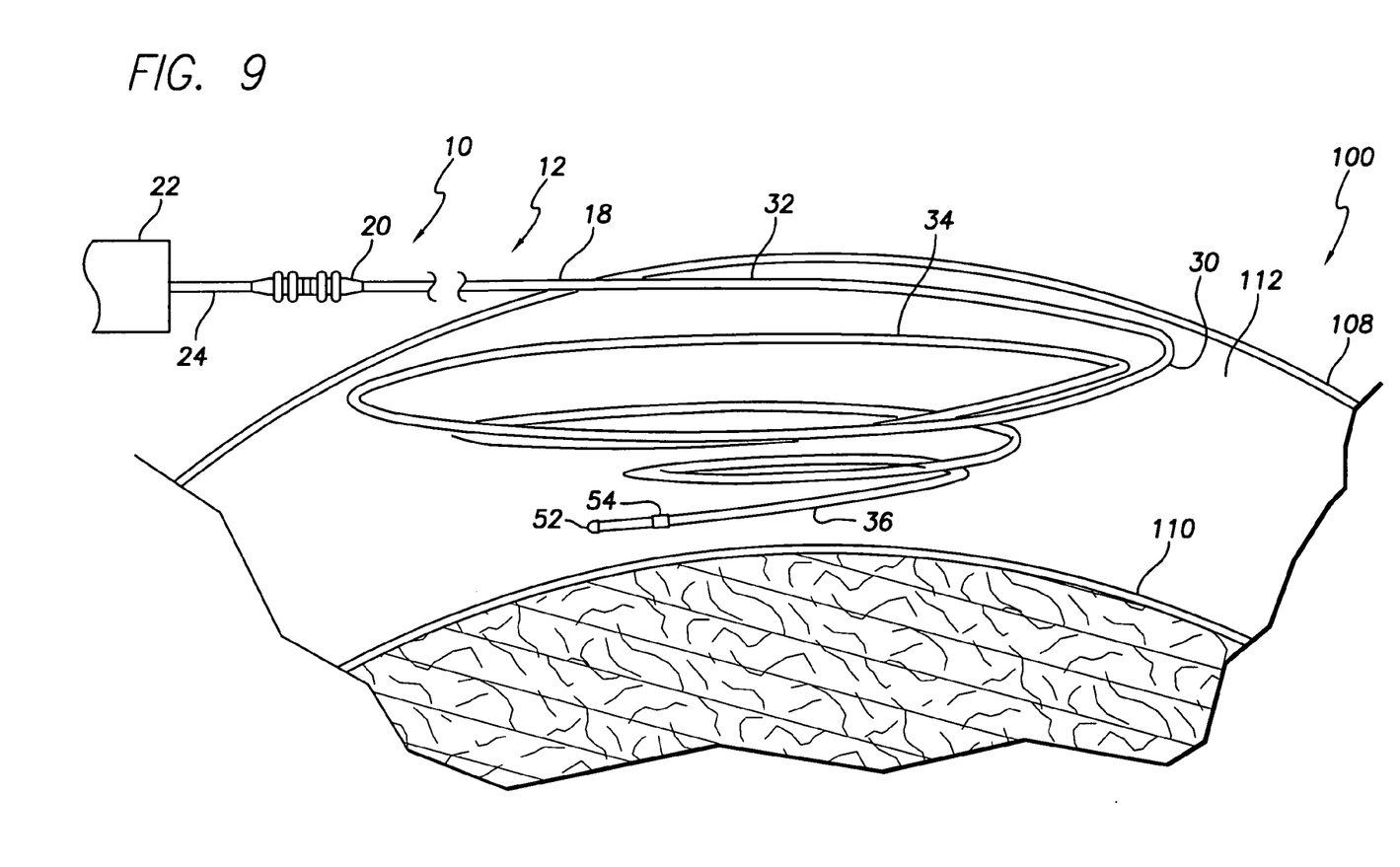
FIG. 9 is a schematic view of a portion of a human heart showing the distal end portion of a lead in accordance with the present invention in place within the pericardial sac.

The lead tip is advanced into the pericardial sac 106 through a small incision or needle puncture 128 in the outer layer 108 thereof. The stylet or guide wire 126 is progressively retracted as the lead is advanced so that the generally conical helical configuration of the wound section of the distal end portion of the lead progressively deployed, taking shape within the pericardial sac 106. It will be seen from FIG. 9 that when deployed within the pericardial sac 106, the generally conical helical section 30 is compressed, tending to flatten between the outer and inner wall layers 108 and 110 creating reaction forces against those wall layers; the friction caused by such forces tends to anchor or fix the lead's distal end portion, retaining it in place. The tendency of the preformed section 30 to expand against the walls of the pericardial sac anchors the lead and resists its withdrawal. To further help prevent dislodgement or displacement of the lead, it is preferred that the conical helical distal end portion of the lead comprise at least two full turns. If desired, the anchoring afforded by the wound section 30 of the distal end portion 16 may be supplemented in various ways. The distal end portion 16 of the lead body may be provided with passive fixation or anchoring elements comprising pliable, outwardly projecting tines or nubs and/or preformed humps or sinuous bends (not shown) manufactured into the distal end portion 16 of the lead body and superimposed on the generally conical helical configuration to create still additional biasing for further enhancing the securement of the lead end within the sac. Alternatively, or in addition thereto, a screw-in helix, electrically active or inactive (not shown), may be provided at the lead tip. Such a helix would be screwed into place by the stylet prior to its withdrawal from the lead, in a fashion well known in the art.

Figure 10:
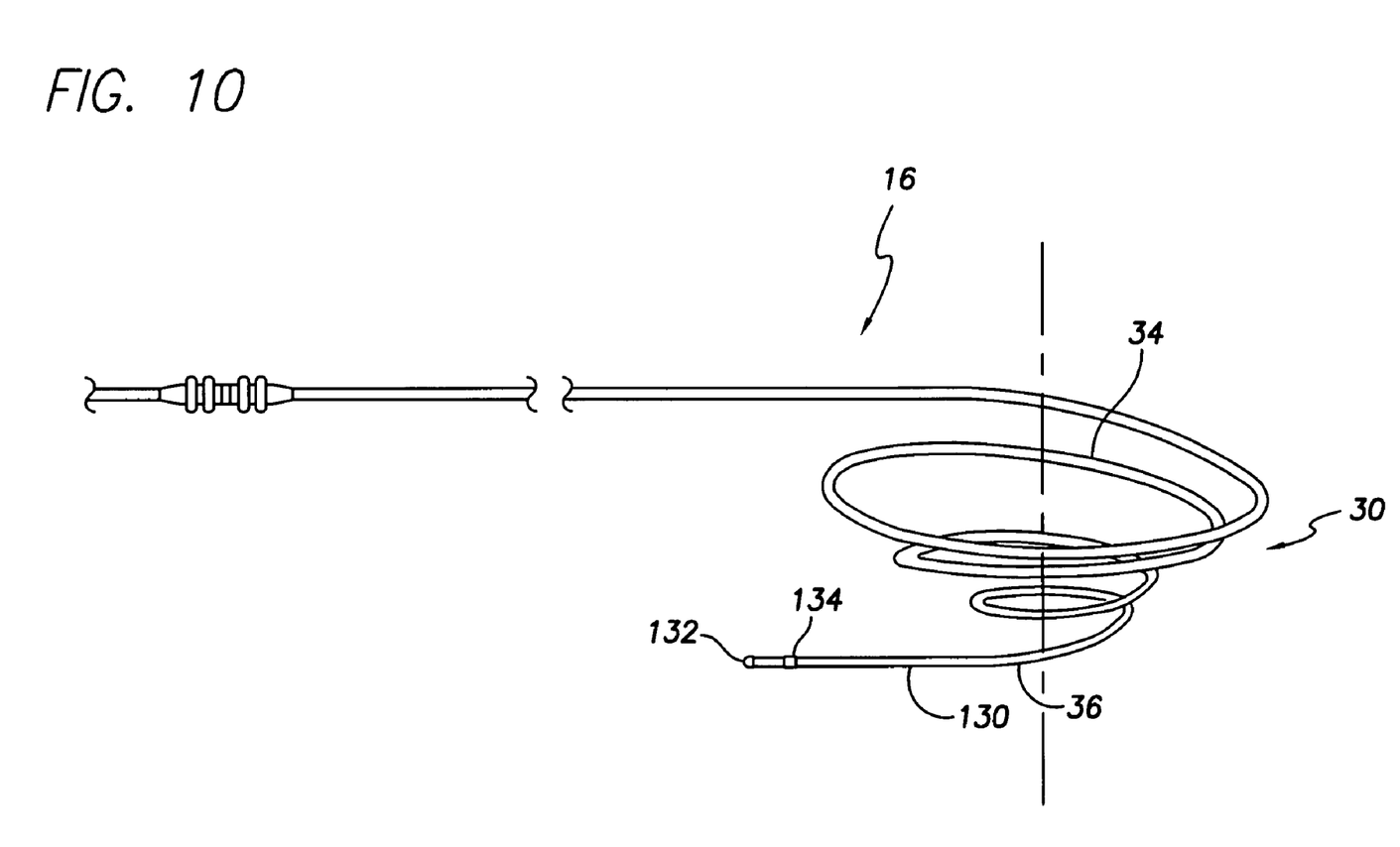
FIG. 10 is a simplified perspective view of a pacing lead in accordance with an alternative embodiment of the present invention.

With reference to FIG. 10, additional resistance to withdrawal of the distal end portion 16 of the lead body from the pericardial sac may be provided by adding to the wound section 30 a length 130 extending from the free end 36 of the wound section and incorporating a tip electrode 132 and a ring electrode 134. The added length 130, shown in FIG. 10 directed toward the connector assembly 20, may be preformed to extend in any direction. In any case, the relatively large conical helical end 34 will resist being withdrawn through the small opening in the outer layer or membrane of the sac while withstanding the rocking motion of the heart.

Figure 11:
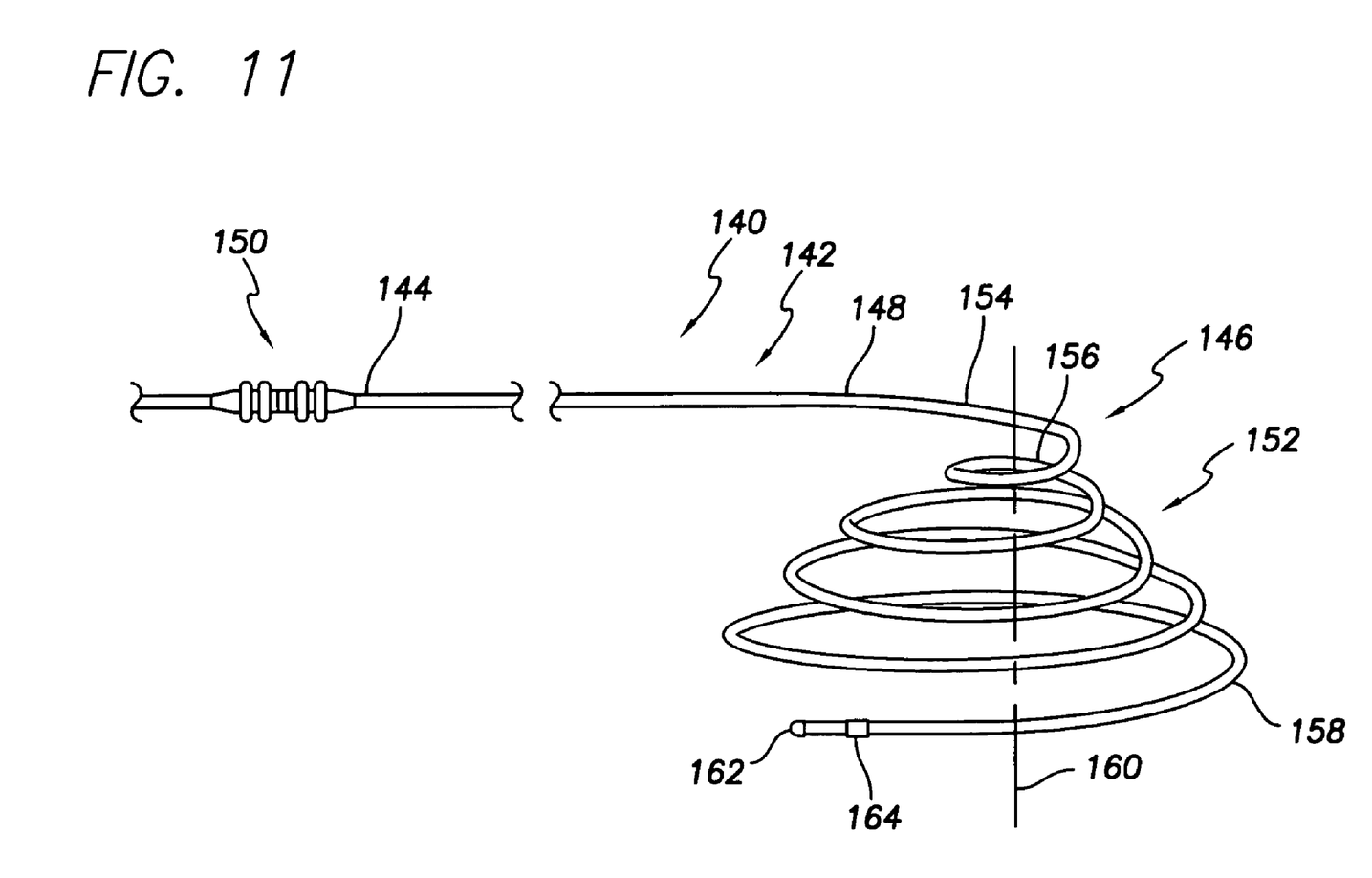
FIG. 11 is a perspective view of a bipolar pacing lead in accordance with yet another alternative embodiment of the present invention.
Figure 12:
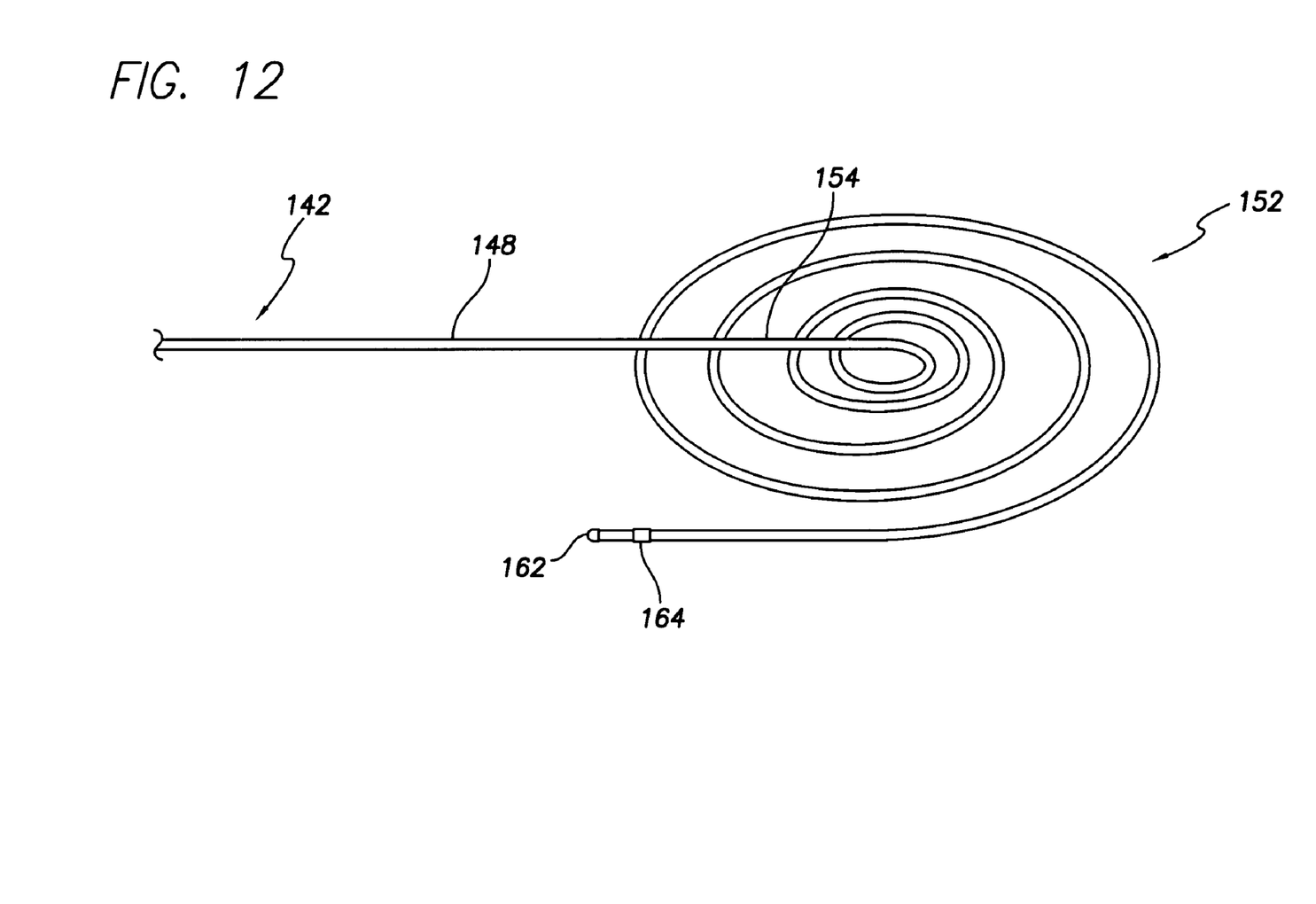
FIG. 12 is a top plan view of a portion of the lead shown in FIG. 11.

Referring to FIGS. 11 and 12, there is shown yet another alternative embodiment of the invention comprising a medical lead 140 including a lead body 142 having a proximal end 144, a distal end portion 146 and an intermediate portion 148 between the proximal end and the distal end portion. The proximal end of the lead body carries a connector assembly 150 of the type described earlier for connecting the lead body to a pacemaker and/or implantable cardioverter-defibrillator (ICD) unit. The distal end portion 146 of the lead body incorporates a multi-turn or wound section 152 extending from a distal end 154 of the intermediate portion 148 of the lead body. As before, the wound section 152 assumes, in a relaxed or unrestrained state, a generally conical, preferably truncated, helical configuration that in plan view resembles a spiral (FIG. 12). The wound section 152 has opposed, first and second ends 156 and 158, respectively, and comprises a plurality of turns about an axis 160 extending through the ends 156 and 158. In this embodiment, the turns of the section 152 becoming progressively larger as they proceed from the first end 156 attached to the distal end 154 of the intermediate portion 148 to the second, free end 158. Accordingly, the embodiment of FIGS. 11 and 12 is an inverted version of the embodiment of FIGS. 1 and 2. Accordingly, as before, the distal end portion 146 of the lead body 142 carries a tip electrode 162 and at least one ring electrode 164 and may also incorporate at least one shocking electrode (not shown) such as that shown and described in connection with FIG. 6. In sum, all of the variations of the previously described embodiments, as well as the associated lead implantation or placement techniques are equally applicable to the embodiment of FIGS. 11 and 12.

As a further variation, the cable conductors or coil conductors may be formed of Nitinol wire preformed into the generally conical helical shape. As is well-known, Nitinol, a nickel-titanium alloy, is characterized by thermal memory. Accordingly, a lead incorporating Nitinol wire may be introduced into the pericardial sac in a straight configuration. The natural heat of the body will raise the temperature of the distal end portion of the lead so that it assumes the conical helical configuration that has been memorized by the material.

It will be evident that the winding sense of the wound section of the various embodiments shown is immaterial; as seen in plan view, the winding sense may be clockwise or counterclockwise.

As shown schematically in FIG. 3, the distal end portion of the lead may include an elution device 170 storing a biologically or pharmacologically active therapeutic agent such as a steroid in the form of, for example, dexamethasone sodium phosphate (DSP) that can be dispensed to infuse the pericardial sac.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. A pericardial lead having a lead body, comprising:
a distal end portion carrying at least one pacing and sensing electrode adapted for placement in the pericardial sac of a human heart, the distal end portion of the lead body including a multi-turn section having opposed ends, opposing forces applied to said ends tending to flatten the multi-turn section, the multi-turn section being thereby adapted for retention within the pericardial sac;
wherein the turns of the multi-turn section become progressively smaller from one end of the section to the other end of the section; and
wherein the at least one electrode is carried adjacent to the end of the multi-turn section having the larger turns.

2. The lead of claim 1 in which:
the multi-turn section has, in a relaxed state thereof, a generally frustoconical configuration.

3. The lead of claim 1 in which:
the at least one electrode comprises a tip electrode at a distal end of the lead body and a ring electrode proximal to the tip electrode.

4. The lead of claim 3 further comprising:
a shocking electrode.

5. A pericardial lead having a lead body, comprising:
a distal end portion carrying at least one pacing and sensing electrode and having a preformed, wound section comprising a plurality of turns and opposite ends, the turns of the wound section becoming progressively smaller along an axis from one end of the wound section to the other end of the wound section, the wound section being adapted to be placed within the pericardial sac of a human heart;
wherein the wound section carries an eluting device for infusing the pericardial sac with a biologically or pharmacologically active agent.

6. The lead of claim 5 in which:
the wound section has, in a relaxed state thereof, a generally frustoconical configuration.

7. The lead of claim 5 in which:
the wound section has, in a relaxed state thereof, a generally truncated conical, helical configuration.

8. The lead of claim 5 in which:
the at least one electrode is carried by the wound section.

9. The lead of claim 8 in which:
the at least one electrode is carried adjacent the end of the wound section having the smaller turns.

10. The lead of claim 5 in which:
an electrical conductor is disposed within the lead body, and the electrical conductor comprises a cable conductor.

11. The lead of claim 5 in which:
an electrical conductor is disposed within the lead body, and the electrical conductor comprises a coil conductor.

12. The lead of claim 5 in which:
an electrical conductor is disposed within the lead body, and the electrical conductor is preformed to define the turns of the wound section.

13. The lead of claim 5 in which:
the lead body comprises an insulative, polymer housing.

14. The lead of claim 5 in which:
one of the ends of the wound section comprises a free end, said free end comprising an additional length extending away from the wound section.

15. The lead of claim 14 in which:
the at least one electrode is carried by the additional length.

16. The lead of claim 5 in which:
the at least one electrode comprises a tip electrode.

17. The lead of claim 5 further comprising:
a shocking electrode.

18. The lead of claim 5 in which:
the wound section comprises Nitinol wire.

19. The lead of claim 5 in which:
the multi-turn section comprises Nitinol wire.

20. The lead of claim 5 in which:
the at least one electrode comprises a tip electrode at a distal end of the lead body and a ring electrode proximal to the tip electrode.

21. The lead of claim 20 further comprising:
a shocking electrode.

22. A pericardial lead having a lead body, comprising:
a distal end portion carrying at least one pacing and sensing electrode and having a preformed, wound section comprising a plurality of turns and opposite ends, the turns of the wound section becoming progressively smaller along an axis from one end of the wound section to the other end of the wound section, the wound section being adapted to be placed within the pericardial sac of a human heart;
wherein the at least one electrode is carried by the wound section; and
wherein the at least one electrode is carried adjacent the end of the wound section having the larger turns.

* * * * *